US00PP22447P3

(12) United States Plant Patent
Eggleton

(10) Patent No.: US PP22,447 P3
(45) Date of Patent: Jan. 3, 2012

(54) *LAVANDULA* PLANT NAMED 'SWEETBERRY RUFFLES'

(50) Latin Name: *Lavandula stoechas*
Varietal Denomination: Sweetberry Ruffles

(76) Inventor: Steve Eggleton, Wonga Park (AU)

( * ) Notice: Subject to any disclaimer, the term of this patent is extended or adjusted under 35 U.S.C. 154(b) by 1 day.

(21) Appl. No.: 12/806,463

(22) Filed: Aug. 13, 2010

(65) Prior Publication Data

US 2011/0047667 P1 Feb. 24, 2011

(51) Int. Cl.
*A01H 5/00* (2006.01)

(52) U.S. Cl. ..... Plt./445

(58) Field of Classification Search ..... Plt./445
See application file for complete search history.

*Primary Examiner* — Susan McCormick Ewoldt

(57) ABSTRACT

A new cultivar of *Lavandula* plant named 'SWEETBERRY RUFFLES' that is characterized by early and repeat flowering, dense plant habit, fragrant flower spikes whose sterile bracts are light peach in color becoming pale pink when fully expanded and aging to vibrant red-purple, and whose fertile flowers are vibrant red-purple in color. In combination these traits set 'SWEETBERRY RUFFLES' apart from all other existing varieties of *Lavandula* known to the inventor.

2 Drawing Sheets

Genus: *LAVANDULA*.
Species: *stoechas*.
Denomination: 'SWEETBERRY RUFFLES'.

BACKGROUND OF THE INVENTION

The present invention relates to a new and distinct cultivar of lavender known botanically as *Lavandula stoechas* and hereinafter referred to by the cultivar name 'SWEETBERRY RUFFLES'.

This application claims the benefit of priority under 35 U.S.C. 119(f) of the application for a grant of Australian Plant Breeders Rights which was filed for the instant plant variety on Aug. 21, 2009 and accepted by the Australian Plant Breeders Rights Office on Dec. 21, 2009 with application number 2009/201.

This application is co-pending with the application for the inventor's variety of *Lavandula stoechas* known as 'STRAWBERRY RUFFLES'(U.S. application Ser. No. 12/806,459). 'SWEETBERRY RUFFLES' and 'STRAWBERRY RUFFLES' arose from the same cross-pollination as described herein.

'SWEETBERRY RUFFLES' is one individual selection in the Australian lavender 'Ruffles Series' that resulted from a formal breeding program. The breeding program was established in November 2001 and conducted by the inventor at the inventor's nursery in Wonga Park, Victoria, Australia. The aim of the breeding program is to develop an ongoing series of *Lavandula stoechas* varieties which are similar in plant form and habit but which bear showy and distinctly different sterile bracts which are the most prominent commercial feature of the species. The species *Lavandula stoechas* is commonly known as Spanish lavender.

The inventor selected 'SWEETBERRY RUFFLES' in 2007 based on a combination of repeat flowering, dense plant habit, sterile bracts which are light peach in color when opening, becoming pale pink when fully expanded and eventually vibrant red-purple when mature. The fertile flowers of 'SWEETBERRY RUFFLES' are vibrant red-purple in color.

'SWEETBERRY RUFFLES' is a selection arising from the controlled cross-pollination of *Lavandula stoechas* 'Winter Lace' (U.S. Plant Pat. No. 18,280) as the female parent, and *Lavandula stoechas* Boysenberry Ruffles (U.S. Plant Pat. No. 18,256) as the male parent. Cross-pollination of the parent plants took place in Wonga Park, Victoria, Australia in November 2005. From this cross the F1 generation was raised in February 2006 and grown to flowering maturity in September 2006. One flowering seedling, to be named 'SWEETBERRY RUFFLES' was isolated in 2006 and planted in a 14 cm container for second year flowering in 2007 at which time 'SWEETBERRY RUFFLES' was confirmed for future commercialization.

'SWEETBERRY RUFFLES' is a perennial suitable for use in containers and in the landscape. Cultural requirements include full sun, adequate but not excess water, and well-draining soil. Mature height is 60 cm. and mature width is 80 cm.

The traits that distinguish 'SWEETBERRY RUFFLES' from the female parent 'Winter Lace' are sterile bract color and plant size at maturity. The sterile bracts of 'Winter Lace' are mauve in color whereas the sterile bracts of 'SWEETBERRY RUFFLES' are light pink in color. A mature plant of 'Winter Lace' is 70 cm in height whereas the mature height of 'SWEETBERRY RUFFLES' is 60 cm.

The trait that distinguishes 'SWEETBERRY RUFFLES' from the male parent 'Boysenberry Ruffles' is length of sterile bracts. The sterile bracts of 'Boysenberry Ruffles' are approximately 1 cm in length whereas the sterile bracts of 'SWEETBERRY RUFFLES' are approximately 2.5 cm in length.

The inventor has observed that the varieties of *Lavandula stoechas* which most closely resemble 'SWEETBERRY RUFFLES' are the inventor's varieties 'Boysenberry Ruffles' and 'Strawberry Ruffles' (co-pending with the instant application).

The trait that distinguishes 'SWEETBERRY RUFFLES' from 'Boysenberry Ruffles' is the length of the sterile bracts as disclosed above relative to 'Boysenberry Ruffles' as male parent.

The traits that distinguish 'SWEETBERRY RUFFLES' from 'Strawberry Ruffles' are color and length of the sterile bracts when fully expanded. The sterile bracts of 'Sweetberry Ruffles' are pale pink in color whereas the sterile bracts of 'SWEETBERRY RUFFLES' are mid pink in color. The sterile bracts of 'Strawberry Ruffles' are approximately 5 mm shorter than the sterile bracts of 'SWEETBERRY RUFFLES'.

'SWEETBERRY RUFFLES' was first asexually propagated by the inventor in 2007. Asexual propagation was accomplished at the inventor's nursery in Australia, and the method utilized was tip cuttings. Since that time 'SWEETBERRY RUFFLES' has been determined stable, and reproduces true to type in successive generations of asexual propagation.

SUMMARY OF THE INVENTION

The following traits have been repeatedly observed and represent the distinguishing characteristics of the new *Lavandula* cultivar named 'SWEETBERRY RUFFLES'. These traits in combination distinguish 'SWEETBERRY RUFFLES' from all other existing varieties of *Lavandula* known to the inventor. 'SWEETBERRY RUFFLES' has not been tested under all possible conditions and phenotypic differences may be observed with variations in environmental, climatic, and cultural conditions, without however, any variance in genotype.

1. 'SWEETBERRY RUFFLES' exhibits dense plant habit.
2. 'SWEETBERRY RUFFLES' exhibits scented flower spikes with sterile bracts that are light peach in color when first open and which become pale pink when fully expanded, and finally age to vibrant red-purple.
3. The fertile flowers of 'SWEETBERRY RUFFLES' are vibrant red-purple in color.
4. 'SWEETBERRY RUFFLES' exhibits early and repeat flowering.
5. 'SWEETBERRY RUFFLES' exhibits fragrant gray-green foliage.
6. Cultural requirements for 'SWEETBERRY RUFFLES' are full sun, adequate but not excess water and well-draining soil.
7. 'SWEETBERRY RUFFLES' exhibits short peduncle length.
8. 'SWEETBERRY RUFFLES' is 60 cm in height and 80 cm. in width at maturity.
9. 'SWEETBERRY RUFFLES' is hardy to USDA Zone 8.

BRIEF DESCRIPTION OF THE DRAWINGS

The accompanying drawings illustrate the overall appearance of the new *Lavandula* cultivar named 'SWEETBERRY RUFFLES' showing the colors as true as it is reasonably possible to obtain in color reproductions of this type.

Color in the drawings may differ from the color values cited in the detailed botanical description, which accurately describe the actual color of the new *Lavandula* variety named 'SWEETBERRY RUFFLES'.

The drawings were made of 1 year old plants which have been grown out of doors in Victoria, Australia.

Figure 1:
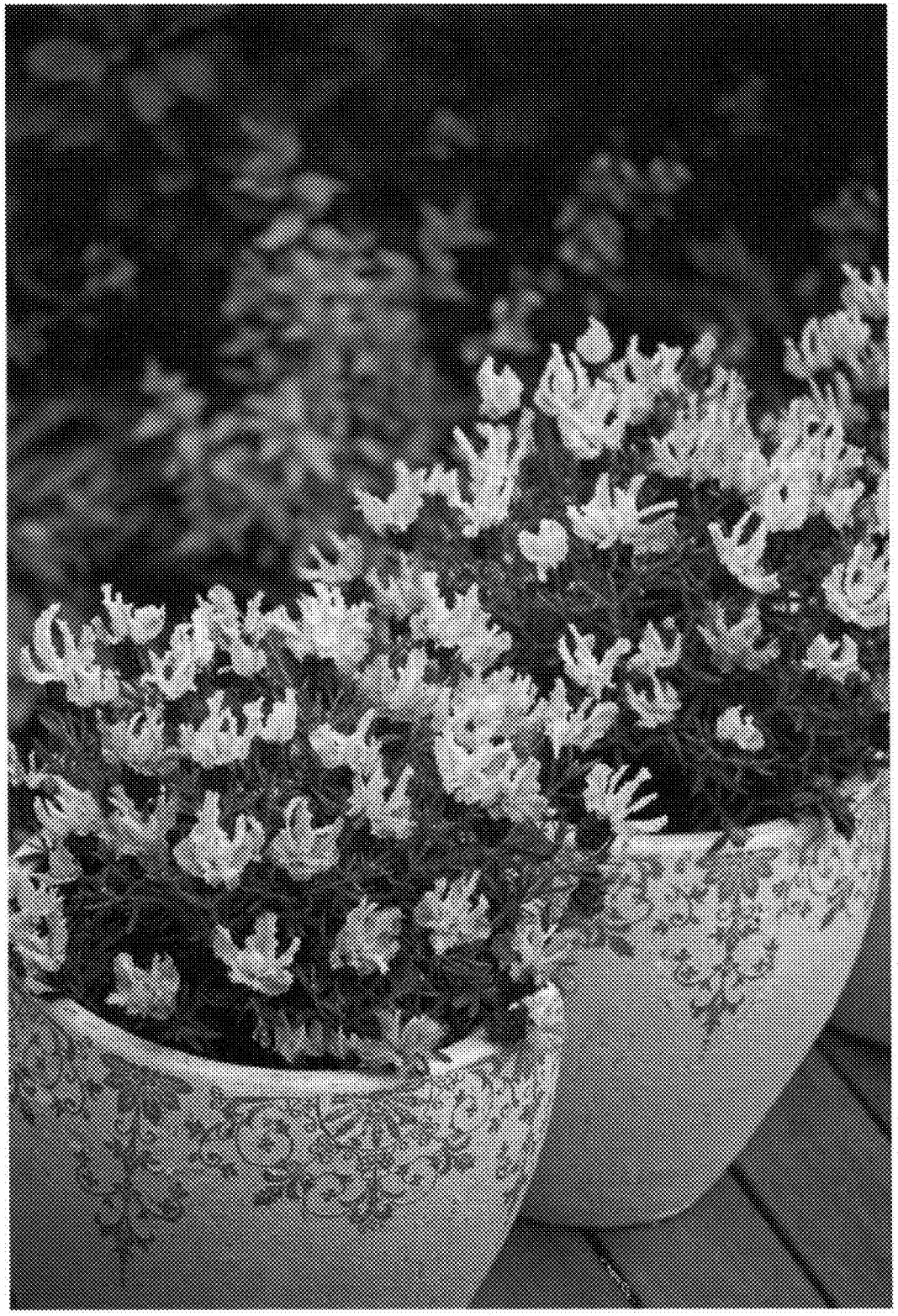

The drawing labeled FIG. 1 depicts two plants in full bloom and growing in a 20 cm diameter container. In this drawing, the sterile bracts of the flower spikes are in their early and mid stages of development, from light peach in color when the bracts are emerging through pale pink when the bracts are fully expanded.

Figure 2:
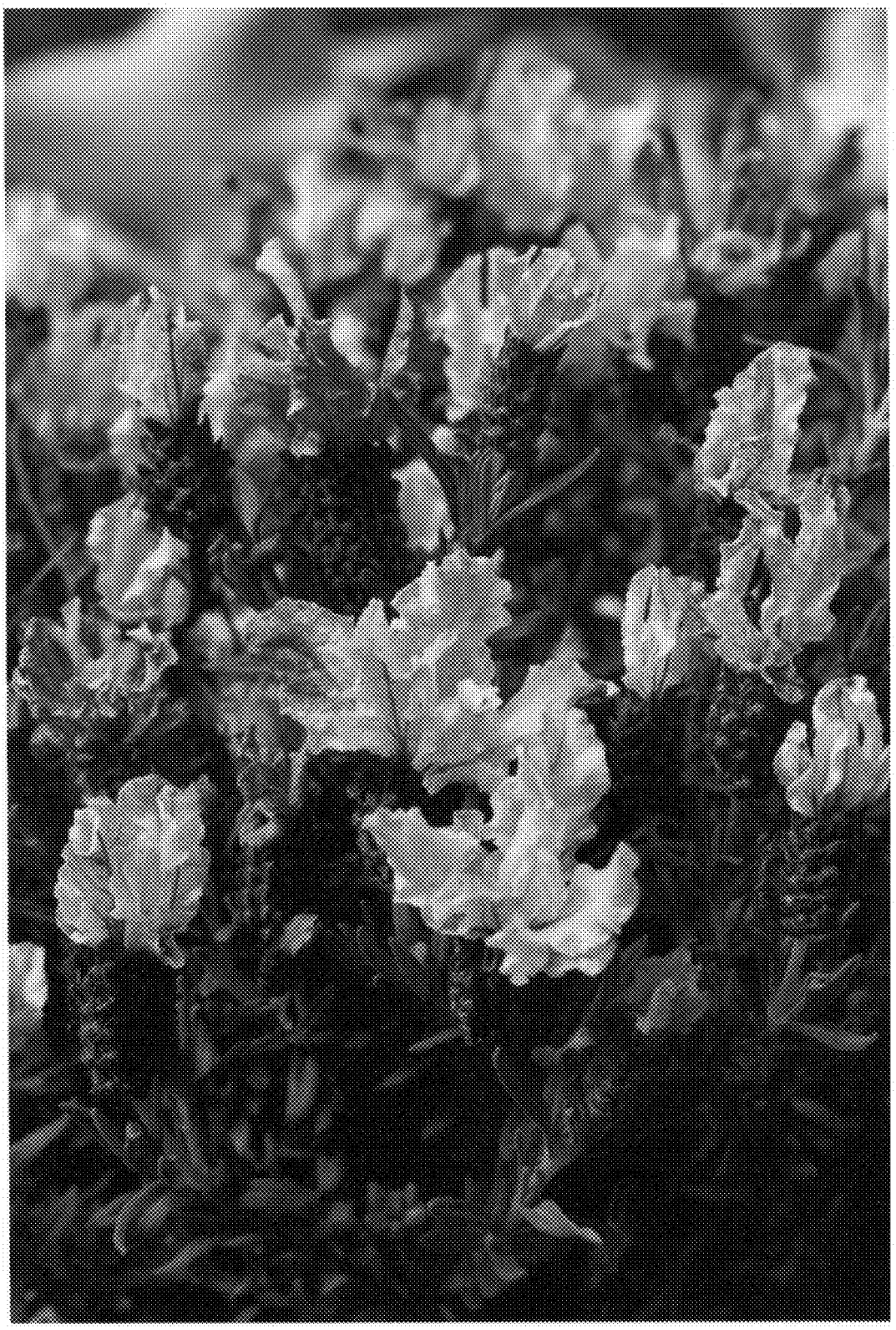

The drawing labeled FIG. 2 depicts a close-up view of the flower spikes in all stages of development of the color of the sterile bracts from light peach through pale pink (i.e. the stages illustrated in FIG. 1) together with some bracts which are mature and vibrant red-purple immediately prior to senescence.

Both drawings were made using conventional techniques and although the leaf and flower colors may appear different from the actual colors due to light reflectance, they are as accurate as possible by conventional photography.

BOTANICAL DESCRIPTION OF THE PLANT

The following is a detailed botanical description of the *Lavandula* cultivar named 'SWEETBERRY RUFFLES'. Data was collected in Santa Barbara, Calif. from 1 year old plants which have been grown out of doors. Color determinations are made in accordance with The 2007 Royal Horticultural Society Colour Chart of London, England, except where general color terms of ordinary dictionary significance are used. The growing requirements are similar to the species.

Classification:

*Botanical classification.*—*Lavandula stoechas* 'SWEETBERRY RUFFLES'.
*Family.*—Lamiaceae.
*Genus.*—*LAVANDULA.*
*Species.*—*stoechas.*
*Variety denomination.*—'SWEETBERRY RUFFLES'.
*Common name.*—Lavender.

Plant:

*Habit.*—Dense.
*Height* (*at maturity*).—60 cm.
*Width* (*at maturity*).—80 cm.
*Life cycle.*—Perennial.
*Use.*—Ornamental for container or landscape.
*Vigour.*—Moderate.
*Hardiness.*—USDA Zone 8.
*Propagation.*—Tip and stem cuttings.
*Root system.*—Fibrous.
*Cultural requirements.*—Full sun, adequate but not excess water, and well-draining soil.
*Time to produce a rooted cutting.*—4-6 weeks.
*Time to produce a* 10 *cm. container plant in bloom.*—20 weeks.
*Seasonal interest.*—Flower spikes in spring and summer.
*Parentage.*—*Lavandula stoechas* 'SWEETBERRY RUFFLES' is a selection that resulted from controlled cross-pollination of the following parents: Female parent plant: *Lavandula stoechas* 'Winter Lace'. Male parent plant: *Lavandula stoechas* 'Boysenberry Ruffles'.
*Disease and insect resistance.*—Minimal disease and insect susceptibility with occasional aphids on new growth.

Stem:

*Branching.*—Upright.
*Stem shape.*—Quadrangular.
*Stem surface.*—Pubescent.
*Pubescence color.*—156D.
*Stem color.*—Juvenile or soft new growth 143D; becoming 178C when semi-ripe and 166C towards the base.
*Stem length.*—Range of 8 cm to 10 cm.
*Stem width.*—3 mm.
*Stem fragrance.*—Resinous scent.
*Internode length.*—Range of 0.50 cm. to 1.50 cm.

Foliage:

*Leaf arrangement.*—Combination of whorled and opposite.
*Leaf division.*—Simple.
*Leaf shape.*—Elongated oblong.
*Leaf margin.*—Entire.
*Leaf apex.*—Apiculate and acute individually present.
*Leaf base.*—Truncate.
*Leaf attachment.*—Sessile.
*Leaf color* (*adaxial surface*).—138C.
*Leaf color* (*abaxial surface*).—138B.
*Leaf surface* (*adaxial and abaxial surfaces*).—Pubescent.
*Color of hairs.*—156D.
*Venation.*—Reticulate.
*Vein color* (*adaxial surface*).—138c.
*Vein color* (*abaxial surface*).—138B.
*Leaf length.*—Range of 1.75 cm. to 4 cm.
*Leaf width.*—Range of 0.20 cm. to 0.70 cm.
*Leaf fragrance.*—Resinous scent.

Inflorescence:

*Fragrance.*—Resinous scent.
*Blooming period.*—April through August.
*Inflorescence type.*—Spike bearing sterile bracts above.
*Spike length.*—3.5 cm.
*Spike diameter.*—2.0 cm.
*Spike shape.*—Cylindrical.
*Inflorescent quantity.*—Range of 65-70 per container plant.
*Peduncle length.*—4.20 cm.
*Peduncle width.*—2 mm.
*Peduncle shape.*—Quadrangular.
*Peduncle color.*—*N*144D.
*Peduncle surface.*—Tomentose.
*Bud dimensions.*—3 mm in length and 1.50 mm in width.
*Bud shape.*—Ovoid.
*Bud color.*—146B.
*Bud surface.*—Lanate.
*Bud apex.*—Acute.

Flowers (fertile bracts):

*Number.*—80-100 on an individual spike.
*Corolla color.*—*N*74A.
*Corolla shape.*—Salverform.
*Corolla depth.*—7 mm.
*Corolla diameter.*—5 mm.
*Corolla tube depth.*—4 mm.
*Corolla tube diameter.*—1.50 mm.
*Petals.*—Four in number.
*Petals fused or unfused.*—Basally fused.
*Petal shape.*—Orbicular.
*Petal length.*—1.50 mm.
*Petal width.*—1.50 mm.
*Petal apex.*—Obtuse and emarginated petal apices individually observed on an individual corolla.
*Petal margin.*—Entire.
*Petal surfaces* (*adaxial and abaxial*).—Glabrous.
*Petal color* (*adaxial and abaxial surfaces*).—N74A.
*Calyx color.*—137A.
*Calyx shape.*—Tubular.
*Calyx surface.*—Lanate.
*Calyx length.*—5 mm.
*Calyx width.*—2 mm.
*Sepals.*—Four in number.
*Sepals fused or unfused.*—Fused along three quarters of the length.
*Sepal apex.*—Acute.

Flowers (sterile bracts):

*Sterile bracts.*—Range of 4-5 per inflorescence.
*Sterile bract form.*—Petaloid.
*Sterile bract appearance.*—Iridescent.
*Sterile bract arrangement.*—Whorled.
*Sterile bract surfaces* (*abaxial and adaxial*).—Smooth, matte.
*Sterile bract shape.*—Broadly oblanceolate.
*Sterile bract margin.*—Entire.
*Sterile bract length.*—Average 2.5 cm.
*Sterile bract width.*—From a maximum of 8 mm (at one-third of the length from the base) tapering to 5 mm close to the apex.
*Sterile bract apex.*—Broadly acute.
*Sterile bract base.*—Aequilateral.
*Sterile bract color* (*abaxial and adaxial surfaces*).—From emergence until fully expanded: Between 29C and 179D. Fully expanded: 65D or paler, becoming N74A immediately prior to senescence.
*Vein pattern.*—Reticulate.
*Vein color* (*abaxial and adaxial surfaces*).—Emerging bracts: 179B. Fully developed bracts: N74A.

Reproductive organs:

*Stamens.*—Four in number.
*Stamen form.*—Adnate to ventral surface of corolla tube.
*Stamen color.*—155C.
*Stamen length.*—5 mm.
*Anther.*—Four.
*Anther color.*—161A.
*Pollen color.*—161C.
*Pollen quantity.*—Moderate.
*Pistil.*—One.
*Pistil length.*—3 mm.
*Pistil color.*—155B.
*Stigma height.*—Less than 0.50 mm.
*Stigma surface.*—Glossy.
*Stigma shape.*—Orbicular.
*Stigma color.*—79A.
*Ovary dimensions.*—Less than 0.50 mm.
*Ovary shape.*—Globose.
*Ovary color.*—138A.
*Ovary position.*—Superior.

Seed: No seed has been observed to date

The invention claimed is:

1. A new and distinct variety of *Lavandula* plant named 'SWEETBERRY RUFFLES' as described and illustrated herein.

* * * * *